United States Patent
Nguyen et al.

(10) Patent No.: US 6,203,547 B1
(45) Date of Patent: Mar. 20, 2001

(54) VASO-OCCLUSION APPARATUS HAVING A MANIPULABLE MECHANICAL DETACHMENT JOINT AND A METHOD FOR USING THE APPARATUS

(75) Inventors: Kim Nguyen, San Jose; Henry Bourang, Turlock; Uriel Hiram Chee, San Carlos, all of CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

(21) Appl. No.: 08/994,104

(22) Filed: Dec. 19, 1997

(Under 37 CFR 1.47)

(51) Int. Cl.⁷ ...................................... A61B 17/58
(52) U.S. Cl. ..................... 606/102; 606/108; 623/1.11
(58) Field of Search ................... 606/108; 623/1.11

(56) References Cited

U.S. PATENT DOCUMENTS

| | | |
|---|---|---|
| 3,834,394 | 9/1974 | Hunter et al. . |
| 3,868,956 | 3/1975 | Alfidi et al. . |
| 5,007,914 * | 4/1991 | Sepetka ........................ 606/108 |
| 5,109,867 | 5/1992 | Twyford, Jr. . |
| 5,122,136 | 6/1992 | Guglielmi et al. . |
| 5,217,484 | 6/1993 | Marks . |
| 5,234,437 | 8/1993 | Sepetka . |
| 5,250,071 | 10/1993 | Palermo . |
| 5,261,916 | 11/1993 | Engelson . |
| 5,263,964 | 11/1993 | Purdy . |
| 5,304,195 | 4/1994 | Twyford, Jr. et al. . |
| 5,312,415 * | 5/1994 | Palermo ........................ 606/108 |
| 5,350,397 * | 9/1994 | Palermo et al. ................ 606/108 |
| 5,354,295 | 10/1994 | Guglielmi et al. . |
| 5,423,829 * | 6/1995 | Pham et al. ................... 606/108 |
| 5,445,646 | 8/1995 | Euteneuer et al. . |
| 5,522,836 * | 6/1996 | Palermo ........................ 606/108 |
| 5,540,680 * | 7/1996 | Guglielmi et al. ............. 606/108 |
| 5,545,169 * | 8/1996 | Varger ........................ 606/108 |
| 5,562,698 | 10/1996 | Parker . |
| 5,578,074 * | 11/1996 | Mirigian ....................... 606/108 |
| 5,624,449 | 4/1997 | Pham et al. . |
| 5,989,242 | 11/1999 | Saadat et al. . |

FOREIGN PATENT DOCUMENTS

| | | |
|---|---|---|
| 0 717 961 A1 | 6/1996 | (EP) . |
| 0 717 969 A2 | 6/1996 | (EP) . |
| 2 696 636 | 4/1994 | (FR) . |
| 2 712 797 | 3/1996 | (FR) . |
| WO 93/21830 | 11/1993 | (WO) . |
| WO 94/06502 | 3/1994 | (WO) . |

OTHER PUBLICATIONS

Anderson et al., "Transcatheter Intravascular Coil Occlusion of Experimental Arteriovenous Fistulas" (1977).
BALT Extrusion (France), "Mechanical Detachment System for SPIRALE," Sales Brochure (1993).

* cited by examiner

Primary Examiner—Paul J. Hirsch
(74) Attorney, Agent, or Firm—Morrison & Foerster LLP

(57) ABSTRACT

A coil-delivery device (20) for delivery of a vaso-occlusion coil (11) to a vascular target site via a catheter (12) is disclosed. The device includes a wire (22) adapted to be slidable received within the lumen (18) of a catheter (12) or an introducer (34), the wire (22) having at its distal end a stiff wavy wire (28) segment adapted to frictionally and releasably engage a vaso-occlusion coil (11) by the end-region inner lumen of the vaso-occlusion coil. Also disclosed are a catheter assembly employing the coil-delivery the device, and a method of releasably engaging a vaso-occlusion coil with the device.

17 Claims, 3 Drawing Sheets

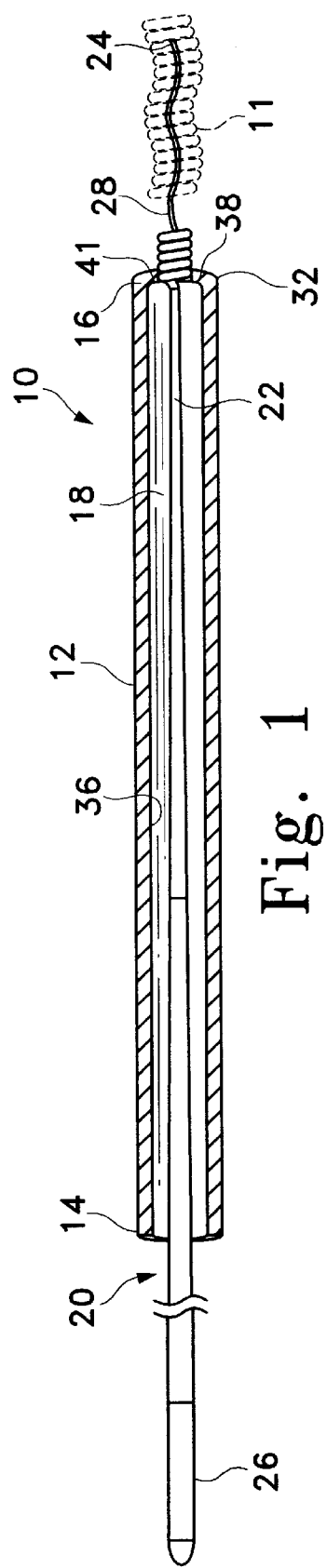
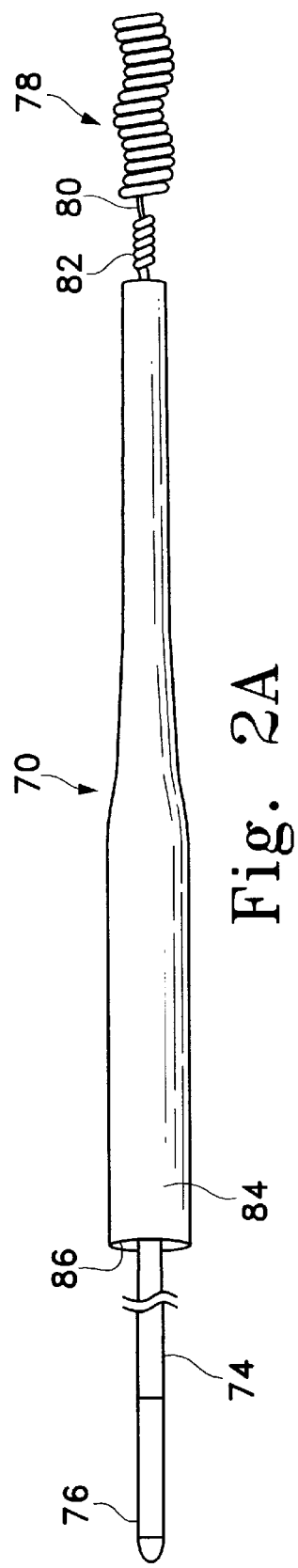
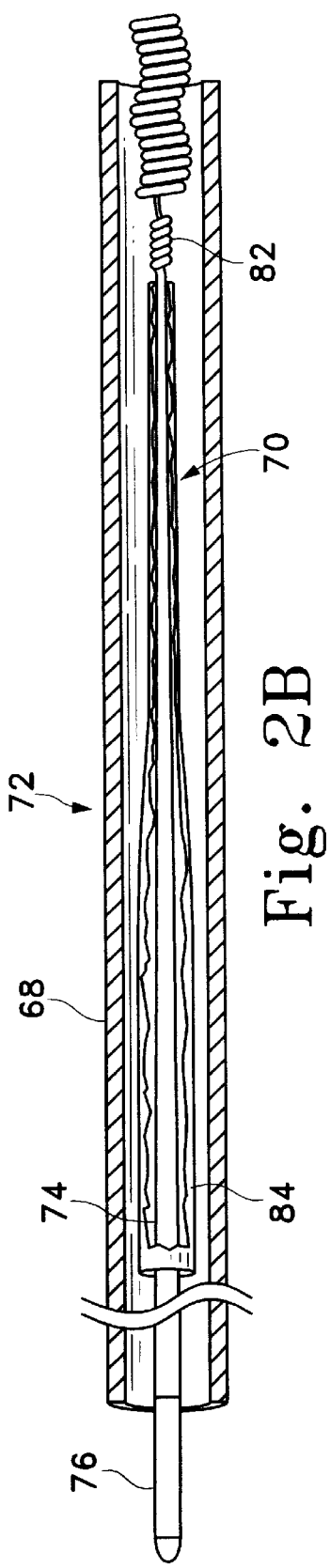

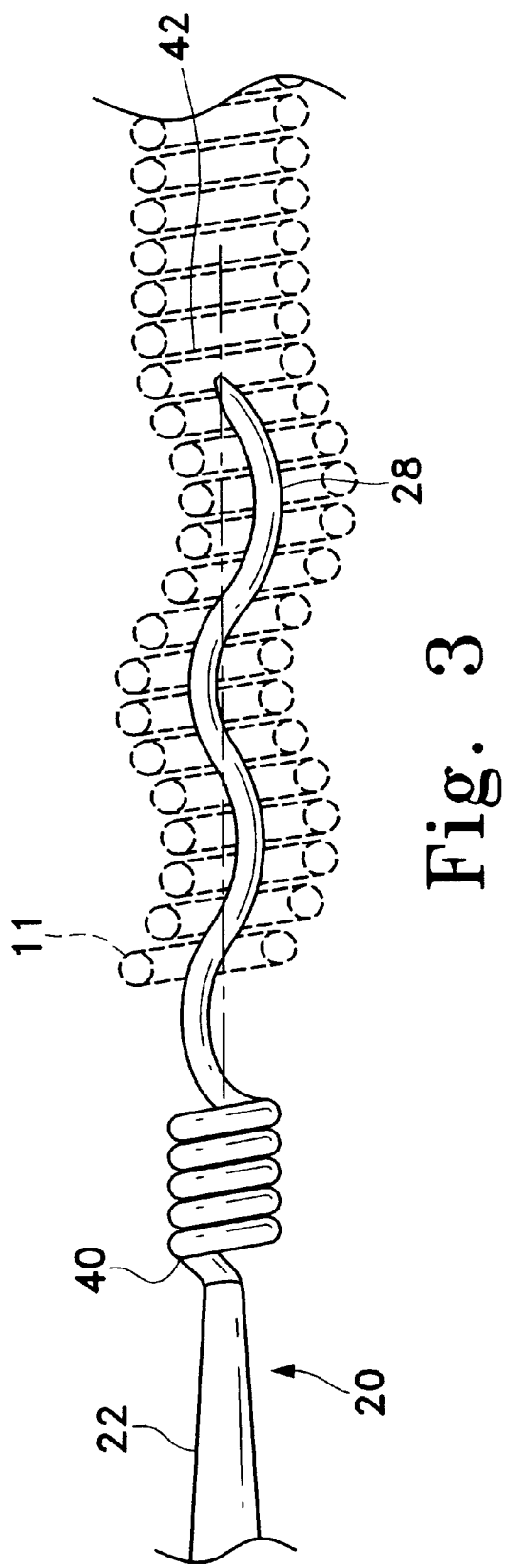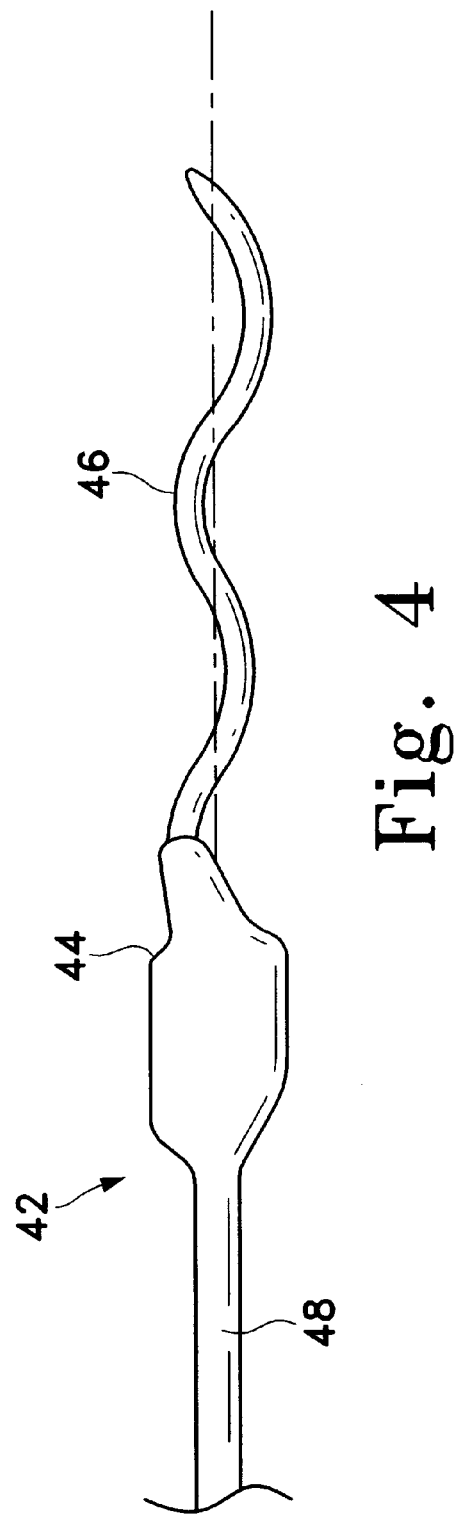

VASO-OCCLUSION APPARATUS HAVING A MANIPULABLE MECHANICAL DETACHMENT JOINT AND A METHOD FOR USING THE APPARATUS

FIELD OF THE INVENTION

A coil-delivery device for delivery of a vaso-occlusion coil to a vascular target site via a catheter is disclosed. The device includes a wire adapted to be slidably received within the lumen of a catheter or an introducer, the wire having at its distal end a stiff, wavy wire segment adapted to frictionally and releasably engage a vaso-occlusion coil by the end-region inner lumen of the vaso-occlusion coil. Also disclosed are a catheter assembly employing the coil-delivery the device and a method of releasably engaging a vaso-occlusion coil with the device.

BACKGROUND OF THE INVENTION

In a variety of medical procedures, a physician may need to occlude vessels in order to contain bleeding or reduce the risk of hemorrhaging.

There are a variety of devices that have been developed to occlude blood vessels. One of these employs a catheter to deliver one or more vaso-occlusion coils to a vascular target site. The vaso-occlusion coils are typically platinum or other surgical-metal coils that are delivered via a vascular catheter. Typically, the coil is placed in a linear condition in the catheter, and is pushed from the end of the catheter by a pusher wire. As the coil exits the delivery device it assumes a relaxed, convoluted shape at the vascular site.

The coil may be deployed simply by ejecting it from the distal end of the catheter. However, this technique may be unsatisfactory where it is desired to better position the coil in the vessel once it has been ejected from the catheter and has assumed its convoluted shape. To overcome this problem, various release mechanisms have been proposed to allow for positive release of the coil from the end of a pusher wire once the coil is properly positioned at the vascular site. Expandable jaw clamps and electrolytically erodible joints are examples of such mechanisms.

It would be advantageous to provide a coil delivery device and catheter assembly which provides the combined advantages of (i) a coil release mechanism that allows for simple coil loading and release, (ii) positive release once the coil is properly positioned at the target site, (iii) multiple reloading steps for placement of multiple coils at a selected target site, and (iv) operable with coils having a variety of coil diameters.

SUMMARY OF THE INVENTION

In one aspect, the invention includes a coil-delivery assembly for delivery of a plurality of vaso-occlusion coils to a vascular target site. The assembly includes (a) an inner-lumen catheter, (b) an introducer for holding a vaso-occlusion coil in a substantially linear condition, (c) a coil-delivery device for releasably engaging a coil in the introducer and transferring the coil into and through the catheter, and (d) a structure for disengaging the coil, with such advanced through the catheter at the distal end thereof, to effect coil release from the delivery device.

The introducer has an end region adapted to be mated with the proximal end of the catheter for transferring a coil from the introducer into the catheter. The delivery device has a wire adapted to be advanced axially within the lumen of the catheter. This wire has a proximal end region adapted to be manipulated to advance the wire within the catheter, and a distal end region having engagement structure adapted to releasably engage the end region of vaso-occlusion coil, with the coil held in the introducer. In one embodiment, each coil has an end-region inner lumen and the engagement structure includes a stiff wavy wire segment for frictionally engaging said inner lumen.

The structure for disengaging the coil from the delivery device may include a one-way valve at the catheter's distal end that permits the coil to be advanced in an inside-to-outside direction only, with coil release being effected by slight retraction of the delivery device. Alternatively, the device may include an outer sleeve through which the wire in the device can be moved axially by manipulating the proximal end of the wire. In this embodiment, the coil-disengaging structure includes a distal sleeve end adapted to engage the coil, as the wire is retracted into the sleeve, to dislodge the coil from the wire.

Multiple coils used in the assembly may each be supplied in a tube having an open access end, where the introducer is adapted to mate with the access end, for transferring a coil from a tube to the introducer.

In another aspect, the invention includes a coil-delivery device for delivery to a vascular target site via an inner-lumen catheter, an elongated, flexible vaso-occlusion coil having an end-region inner lumen. The device includes a wire adapted to be advanced axially within the lumen of the catheter. The wire has a proximal end region adapted to be manipulated to advance the wire within the catheter, and a distal end region forming or attached to a stiff wavy wire segment adapted to frictionally and releasably engage the vaso-occlusion coil by insertion of the wavy wire segment into the end-region inner lumen of the coil. The device is used to advance the coil into and through a catheter and to allow positive release of the coil once it has been properly positioned at the target site.

The wire may have a radial enlargement adjacent the wavy wire segment to limit axial movement of the wire into the coil's inner lumen. The wavy wire segment may have a substantially sinusoidal shape extending at least one full wave cycle, where the ratio of wave amplitude to wavelength is, for example, between about 0.05 to 0.3. The frictional engagement between the wavy wire segment and the vaso-occlusive coil may be such as to require a force of at least about 0.1 lbs to disengage.

In one general embodiment, the wire is designed for use with a catheter having a distal end one-way valve that permits the coil to be advanced in an inside-to-outside direction only. The coil is released by retracting the wire into the catheter once the coil has been expelled from the catheter end.

In another general embodiment, the delivery device further includes an outer sleeve through which the wire in the device can be axially moved by manipulating the proximal wire end. The sleeve has a distal end adapted to engage the coil, as the wire is retracted into the sleeve, to dislodge the coil from the wire.

Also disclosed is a method for releasably engaging a vaso-occlusion coil of the type having an end-region inner lumen. The method involves the steps of immobilizing the coil in a substantially linear condition in a tube having an open access end and inserting into the tube a wire device of the type described above.

These and other objects and features of the invention will become more fully apparent when the following detailed description of the invention is read in conjunction with the accompanying drawings.

BRIEF DESCRIPTION OF THE DRAWINGS

FIG. 1 is a partial cross-sectional view of a catheter and coil delivery device in a coil delivery assembly constructed according to one embodiment of the invention.

FIGS. 2A and 2B show a coil delivery device constructed in accordance with another embodiment of the invention.

FIG. 3 is an enlarged view of the distal end region of a delivery device constructed according to one embodiment of the invention.

FIG. 4 shows the distal end region in an alternative embodiment of a delivery device of the invention.

DETAILED DESCRIPTION OF THE INVENTION

Figure 5:
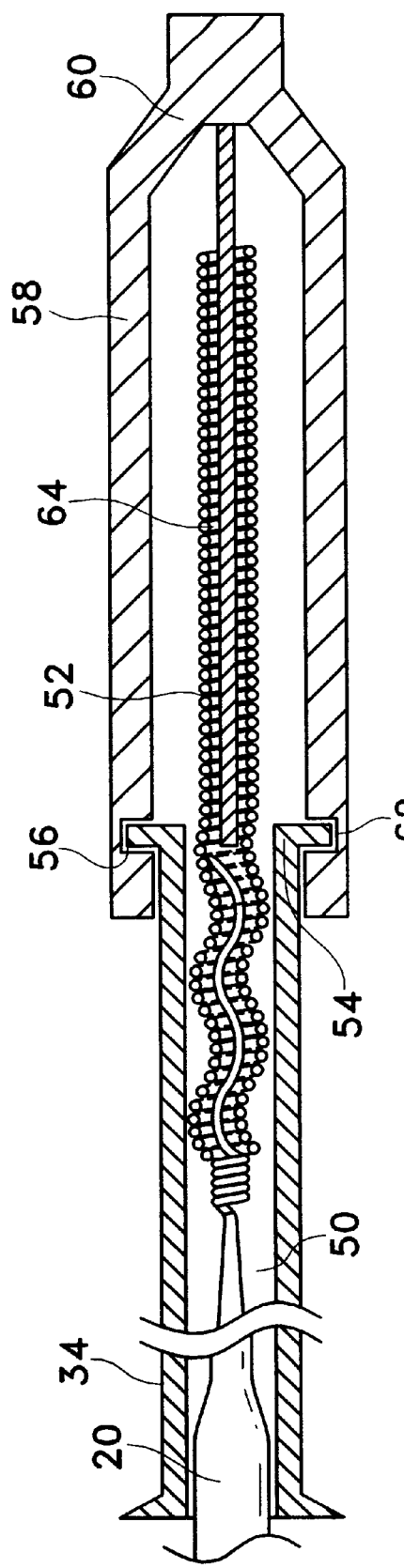
FIG. 5 is a partial cross sectional view of a delivery device and introducer used in transferring a coil from a supply tube to the introducer.

FIG. 1 illustrates components of one embodiment of a coil-delivery assembly 10 for delivering one or more coils, such as coil 11, to a vascular target site. The assembly includes a catheter 12 having proximal and distal ends 14, 16, respectively, and an inner lumen 18 extending therebetween.

A coil-delivery device 20 in the assembly is formed of a wire 22 having distal and proximal ends 24, 26, respectively. The distal end region of the wire takes the form of a stiff wavy wire segment 28 which is constructed to releasably engage a vaso-occlusive coil, such as coil 11, in a manner described below. The wire is adapted to be advanced axially within the catheter to place the wavy wire segment 28 and attached coil beyond the catheter's distal end, by manipulation of the wire's proximal end, which projects beyond the proximal end of the catheter, as shown. This wire segment 28, which serves to releasably engage the end-region of a coil in a manner described below, is also referred to herein as engagement means.

The assembly also includes structure or means 32 for disengaging a coil, such as coil 11, with such advanced through the catheter's distal end, to effect coil release from the wire segment, when the wire is retracted within the catheter. In the embodiment shown in FIG. 1, this engaging structure or means takes the form of a one-way valve 32 formed on the distal catheter end 16.

Also included in the assembly is an introducer (shown at 34 in FIGS. 5 and 6) for use in introducing a coil, such as coil 11, carried on device 20 into the catheter, in a manner to be described.

Considering now details of the assembly, catheter 12 may be a conventional single-lumen catheter for use in accessing a vascular target site, e.g., along tortuous-path, narrow vessels. The catheter is formed of a flexible tubing 36, typically about 100–300 cm in length, which may have a reduced thickness and/or stiffness on progressing from the proximal to distal ends to allow improved target site accessing in deep tissue. The inner diameter of the catheter, i.e., lumen diameter, may vary in size according to the size of the coil to be delivered. Typical catheter cross-sectional dimensions are between about 25–100 mils inner diameter and between about 5–20 mils tubing wall thickness. The catheter's inner wall may have a lubricious coating to improve the ease of movement of device 20 and a coil carried thereon through the catheter.

Valve 32 formed at the distal end of the catheter is an annular ring 38 which may be formed integrally with tubing 36, and which defines a relaxed-condition opening 41. The ring is flared outwardly, as shown, and is somewhat flexible, allowing it to accommodate passage of a coil, such as coil 11, through opening 41 by slight outward expansion of the ring and opening 40. Opening 40 is, however, smaller than the outer diameter of a coil, and a force exerted on ring 38 from an outside-to-inside direction causes the ring opening to become still smaller, so that it effectively blocks movement of the coil from an outside-to-inside direction (right-to-left) in FIG. 1. Wire 22 in device 20 can be, for example, a flexible torqueable guide wire having a total length between about 100–300 cm and a maximum diameter of the wire between about 8–30 mils (thousandths of an inch). The body portion of the wire may have a substantially constant diameter along its length, or may contain regions of taper. In one embodiment, the wire has a tapered distal portion of about 5–50 cm in length, and preferably about 15–20 cm in length, with the body portion making up the remainder of the length of the wire. The taper is preferably such as to reduce the diameter of the wire from about 8–30 mils at the proximal end to a minimum diameter of typically 1–5 mils at the distal wire end. Stainless steel wire of suitable for making device 20 type is commercially available, e.g., from Wytech and National Standard.

The distal end segment of the wire and the wavy wire 28 may be tapered and molded by wire grinding, drawing, punching, stamping or etching techniques. The advantages of the grinding method for tapering the wire are accurate control over the depth of cut along the wire and the ability to produce the continuous taper at any region along the length of the wire. Etching techniques for etching stainless steel substrates are also known for use with the present invention. Punching or stamping may be preferred to permanently shape the stiff wavy wire for frictional and releasable engagement of the proximal-end lumen of a coil. As shown in FIG. 3, the coil-delivery device includes a radial enlargement 40 separating the wavy wire segment from upstream portions of the device. As can be appreciated from FIG. 3, enlargement 40 has a diameter greater than that of inner lumen 42 formed in the end region of coil 11, effectively blocking movement of the coil over segment 28 at the point of the enlargement. At the same time, the enlargement diameter is somewhat smaller than opening 41 in the catheter one-way valve, allowing the enlargement to be moved through the opening in either direction.

With continued reference to FIG. 3, wire segment 28 may be formed integrally with wire 22, with the enlargement 40 being formed as a coil wrapping over the continuous wire. The segment 28 is relatively stiff, meaning that it is capable of holding its wavy shape when engaged with the inner lumen of a coil.

In the embodiment shown, segment 28 has a generally sinusoidal shape extending over at least about 1 full cycle, and shown here extending over about 2 and a half cycles. The diameter of the wire forming segment 28 is preferably about 2–10 mils, and the ratio of wave amplitude, as measured between the highest and lowest wave points in FIG. 3, to wavelength in the wavy wire segment is preferably between about 0.05 to 0.3.

FIG. 4 shows the distal end region of a device 42 terminating at its distal end in a radial enlargement 44 and a stiff wavy wire segment 46. In this embodiment, wire segment 46 is not formed integrally with wire 48 making up the major length of device 20, but is soldered to wire 48 through a solder joint that forms the radial enlargement 44. The solder joint is dimensioned, as above, to pass through opening 41 in the catheter end valve, and block advancement of a coil lumen past the point of the enlargement.

The coil-delivery device just disclosed and as embodied in devices 20 and 42, also form one aspect of the invention.

As indicated above, assembly 10 further includes an introducer for use in transferring a coil from the introducer into the catheter in the assembly. FIG. 5 illustrates such an introducer, indicated here at 34. Introducer 34 defines an inner cylindrical cavity 50 which is open at both ends. The introducer is dimensioned to receive a vaso-occlusion coil, such as coil 52, within the cavity. The introducer's distal end, indicated here at 54, has an annular notch 56 for releasably engaging the open end of a coil-supply tube 58.

In a typical embodiment, where multiple coils are to be delivered, each coil is supplied in a tube, such as tube 58, which is closed at one end and open at its opposite end, here indicated at 60. The open end has an annular groove 62 for receiving notch 56, to engage the introducer by snap-fit and anchor the introducer releasably to the coil-supply tube during a coil-transfer operation.

A variety of coils, such as coil 52, may be suitable. One example of a coil for delivery by the present invention is the "flower coil" available from Target Therapeutics (Fremont, Calif.). This coil can be easily constrained to a linear condition, but will "fold" into a convoluted vaso-occlusion condition when released from its linear constraints. Typical coil lengths are between about 1–5 cm. Typical outer coil diameters are between about 15–35 mils. As seen in FIG. 5, the coil defines an inner lumen 64 extending through the coil. This lumen has typical diameters between and 5 and 25 mils.

Operation of the assembly will now be described with respect particularly to FIGS. 5 and 6. Initially, catheter 12 in the assembly is directed to a selected vascular target site, e.g., using a conventional guide wire to guide the catheter through a vessel path. The guide wire is then removed, leaving the catheter in place to serve as a conduit for delivering coils from the proximal, accessible catheter end to the target site adjacent the catheter's distal end.

To supply the first coil to the target site, a vaso-occlusion coil having a selected length and diameter, e.g., 15–35 mils, is transferred from a supply tube via the intruducer, into the catheter. This is done by attaching the distal end 34 of the intruducer 34 by snap-fit engagement, to a coil-supply tube, such as tube 58. Device 20 is then inserted through the introducer and into the coil-supply tube 58, with the wavy segment of the device entering the end region inner lumen of the coil, as indicated. The device is pushed into the tube until the wavy segment is fully inserted into the coil lumen, i.e., until the enlargement on the wire abuts the free end of the coil. At this point the coil is releasably and frictionally engaged with the wavy segment by virtue of the deformation of the coil over the segment. Preferably, the frictional engagement between the stiff wavy wire segment and the vaso-occlusive coil is such as to require requires a force of at least about 0.1 lbs to disengage. The coil may now be removed from its supply tube and drawn completely into the introducer cavity by retracting the wavy wire segment into and substantially through the introducer.

The introducer 34 is now disengaged from the supply tube and snap-fit engaged with catheter 12 (FIG. 6), which has an end groove 66 similar to groove 62 for snap-fit engagement with the distal end of the introducer. The coil-delivery device is now advanced in the direction of the catheter's distal end, ultimately until the attached coil is pushed through valve 32 in the catheter and out into a vessel lumen, where the coil can assume its convoluted, vaso-occluding condition. The guide wire may be further manipulated at this stage, until the coil is optimally positioned at the target site. When this positioning is achieved, the device is retracted, initially bringing the engaged end of the coil into contact with the face of valve 32 and ultimately dislodging the coil from the wavy wire segment to release the coil at the target site.

The coil-delivery device is then withdrawn from the catheter and a new coil may be (i) transferred from its supply tube to the introducer, (ii) transferred from the introducer to catheter, and (iii) released from the wavy segment at a selected position at the target site, as described above. This reloading and new coil placement at the target site is repeated unto a desired number of coils have been placed at the site.

FIG. 2A shows portions of a coil-delivery device 70 and, in FIG. 2B, as inserted in a coil-delivery assembly 72 constructed in accordance with another embodiment of the invention. The assembly 72 includes, in addition to a catheter and the wire device, an introducer, (similar introducer 34 described above) and structure or means for engaging a vaso-occlusion coil to effect coil release from the device. As will be seen below, this engagement means is formed in the coil-delivery device in this embodiment rather than in the assembly catheter. The catheter employed in this assembly is an inner lumen catheter like catheter 12 except that the distal end of the present catheter has a conventional catheter-tube end and does not include the one-way valve of catheter 12.

Coil-delivery device 70 includes a wire 74 adapted to be advanced axially within the lumen of the catheter. The wire has a proximal end region 76 adapted to be manipulated to advance the wire within the catheter and a distal end region 78 forming a stiff wavy wire segment 80 adapted to frictionally and releasably engage said vaso-occlusion coil, as described above with respect to device 20. As in device 20, the wavy segment 80 is separated from the major proximal length of the wire by a radial enlargement 82 which acts to limit the position of the coil on the wire to the point of the enlargement. The construction of the wire may be substantially as described with respect to wire 22. Device 70 further includes an elongate outer sleeve 84 which extends along a major portion of wire 74, with relatively short distal and proximal portions of the wire extending beyond distal and proximal portions of sleeve, respectively. The sleeve has an inner lumen 86 that accommodates wire 74 therein, including enlargement 82, but is smaller than the outer diameter of a coil to be delivered by the device. The sleeve accommodates at least limited axial travel of the wire between extended and retracted positions as described below.

The outer diameter of sleeve 84 is dimensioned to allow the wire device, including the sleeve, to be advanced axially through the catheter to place the distal end region of the device beyond the distal end of the catheter, for coil placement and release at the target site.

As noted above, the wire can be moved axially within the sleeve between extended and retracted positions by manipulating the exposed proximal portion of the wire. In its extended position, the wavy segment and enlargement extend beyond the sleeve's distal end, and thus allow releasable engagement of a vaso-occlusion coil on the wire device in the manner described above. In its retracted position, the enlargement and wavy segment are retracted into the sleeve's distal end for purposes of releasing a coil carried on the wavy segment from the device. Thus, the structure or means for disengaging the coil for release from the wire in this embodiment includes the distal end of sleeve 84.

Operation of assembly 72 is similar to that of assembly 10 and will be described again with respect to FIGS. 5 and 6, it being recognized that the device 70 in the assembly will be substituted will for device 20 actually shown in the figure.

Initially, as shown in FIG. 2B, catheter 68 in assembly 72 is directed to a selected vascular target site, as above, and the guide wire is removed, leaving the catheter in place to serve as a conduit for coil delivery.

To supply the first coil to the target site, introducer 34 is inserted into the open end of a coil-supply tube, as above. Device 70 is then inserted through the introducer and into the coil-supply tube, with the wavy segment of the device entering the end region inner lumen of the coil. The device is pushed into the tube until the wavy segment is fully inserted into the coil lumen, i.e., until enlargement 82 abuts the free end of the coil. At this point the coil is releasably and frictionally engaged with the wavy segment. The coil may now be removed from its supply tube and drawn completely into the introducer cavity.

Figure 6:
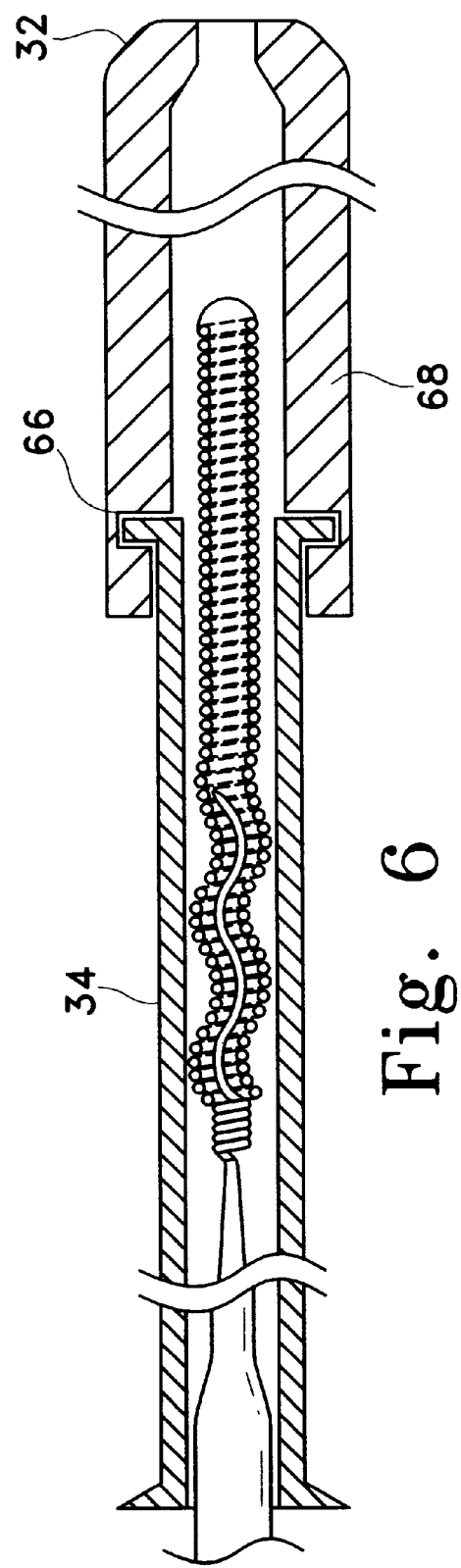
FIG. 6 is a partial cross sectional view illustrating transfer of a vaso-occlusion coil from an introducer into a catheter.

The introducer is disengaged from the supply tube and engaged with catheter 68, e.g., by the snap-fit engagement shown in FIG. 6. The coil-delivery device is now advanced in the direction of the catheter's distal end until the attached coil is advanced beyond the distal end of the catheter, where the coil can assume its convoluted, vaso-occluding condition. The delivery device may be further manipulated at this stage until the coil is optimally positioned at the target site. When this positioning is achieved, wire 74 is retracted with respect to sleeve 84, bringing the engaged end of the coil into contact with the distal end of the sleeve, dislodging the coil from the wavy wire segment as the latter is retracted into the sleeve.

The coil-delivery device is then withdrawn from the catheter and a new coil may be (i) transferred from its supply tube to the introducer, (ii) transferred from the introducer to catheter, and (iii) released from the wavy segment at a selected position at the target site as described above. This reloading and new coil deposition at the target site is repeated until a desired number of coils have been placed at the site.

It will be appreciated that the engagement means in the delivery device for releasably engaging the coil may have a variety of structures other than the wavy wire segment illustrated herein. Engagement means which are capable of gripping a coil, e.g., by a releasable jaw mechanism, are also contemplated.

The method described above for releasably engaging a vaso-occlusion coil of the type having an end region inner lumen is yet another aspect of the invention. The method includes first immobilizing the coil in a substantially linear condition in a tube having an open access end, such as tube 58 described above. There is then inserted into this tube, a wire device having a wire with a proximal end region a distal end region forming a stiff wavy wire segment. This wavy segment is adapted to frictionally and releasably engage the vaso-occlusion coil by insertion of the wavy wire segment into the end-region inner lumen of the coil.

From the foregoing, it will be appreciated how various objects and features of the invention have been met. The wire device allows a coil, e.g., supplied in a supply tube, to be releasably engaged merely by inserting the wire device into the supply tube until full coil engagement with the device's wavy segment occurs. Once releasably attached to the wire device, the coil can be positively manipulated into and through a catheter and released at a selected vascular site simply by retracting a wire in the device. This allows for simple reloading and release of multiple coils during a coil vaso-occlusion procedure.

Further, the wavy segment in the device is adapted to frictionally engage coils having a variety of different lumen sizes; thus, the physician can select a range of coil sizes to be placed without replacing any of the assembly components.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

We claim as our invention:

1. A vaso-occlusion coil delivery assembly comprising:
   (a) a catheter having proximal and distal ends and an inner lumen extending therebetween,
   (b) an introducer for holding a vaso-occlusion coil in a substantially linear condition, said introducer having an end region adapted to be mated with the proximal end of said catheter for transferring said coil from the introducer into the catheter,
   (c) a coil delivery device comprising a wire adapted to be advanced axially within the catheter lumen, said wire having a proximal end region adapted to be manipulated to advance the wire within the catheter and a distal end region having a stiff wavy wire segment adapted to releasably and frictionally engage an end region inner lumen of said vaso-occlusion coil, and
   (d) means for releasably disengaging the coil from said stiff wavy wire segment.

2. The assembly of claim 1 further comprising a vaso-occlusion coil, said coil having an end region lumen.

3. The assembly of claim 2 further comprising a radial enlargement adjacent said stiff wavy wire segment.

4. The assembly of claim 2 wherein said means for releasably disengaging the coil includes, at the catheter's distal end, a one-way valve that permits the coil to be advanced in an inside-to-outside direction only.

5. The assembly of claim 2 further comprising an outer sleeve through which said wire may axially move by manipulation of the proximal end of the wire, and wherein said means for releasably disengaging the coil comprises a distal end of the sleeve, said sleeve distal end adapted to engage said coil as said wire is retracted into the sleeve to dislodge the coil from the wire.

6. The assembly of claim 5 further comprising a radial enlargement adjacent said stiff wavy wire segment to limit axial movement of the wire into the coil lumen, said enlargement having a smaller diameter than an outer diameter of said coil, and wherein a distal end of said sleeve is adapted to block passage of the coil, but not of said enlargement, therethrough.

7. A vaso-occlusion coil delivery device comprising:
   a wire having a proximal end region adapted to be manipulated to advance the wire within a catheter, and a distal end region forming a stiff wavy wire segment adapted to frictionally and releasably engage a vaso-occlusion coil by insertion of the wavy wire segment into a lumen of the coil.

8. The device of claim 7 further comprising a radial enlargement adjacent said stiff wavy wire segment.

9. The device of claim 7 further comprising a vaso-occlusive coil and said catheter, said catheter having a lumen through which said coil may be advanced, said catheter further comprising a distal end one-way valve for permitting the coil to be advanced therethrough in an inside-to-outside direction only.

10. The device of claim 7 further comprising an outer sleeve through which said wire may be axially moved, said sleeve having a distal end adapted to engage said coil, as said wire is retracted into the sleeve, to disengage the coil from the wire.

11. The device of claim 10 further comprising a radial enlargement adjacent said wavy wire segment for limiting axial movement of the wire into the coil's inner lumen, said enlargement having a smaller diameter than an outer diameter of said coil, said sleeve distal end being adapted to block passage of the coil, but not said enlargement, therethrough.

12. The device of claim 7 wherein said wavy wire segment has a substantially sinusoidal shape extending at least one full wave cycle, said cycle having a wave amplitude and a wavelength, and wherein a ratio of the wave amplitude to the wavelength segment is between about 0.05 and 0.3.

13. The device of claim 7 wherein a force of at least about 0.15 pounds is required to disengage the wavy wire segment from the vaso-occlusive coil.

14. A method for releasably engaging a vaso-occlusion coil and deploying said coil to a target vascular site, comprising:
 (a) immobilizing the coil in a substantially linear condition in a tube, said tube having an open end and a lumen,
 (b) inserting a wire into said tube lumen through said tube open end, said wire comprising a proximal end region and a distal end region, said distal end region forming a stiff wavy wire segment,
 (c) frictionally and releasably engaging said coil by inserting the wavy wire segment into a lumen of the coil,
 (d) distally advancing said wire and said engaged coil through said tube lumen and into and through a lumen of a catheter, said catheter being engaged to a distal end of said tube until said coil is outside said catheter lumen,
 (e) proximally withdrawing said wire and attached coil until a proximal end of said coil abuts a distal end of said catheter, and
 (f) continuing to proximally withdraw said wire until said wire is dislodged from said coil lumen to deploy said coil at said target site.

15. The method of claim 14 wherein said wire further comprises a radial enlargement adjacent said stiff wavy wire segment for limiting axial movement of the wire into the coil lumen.

16. The method of claim 14 wherein said wavy wire segment has a substantially sinusoidal shape extending at least one full wave cycle, said cycle having a wave amplitude and a wavelength, and wherein a ratio of the wave amplitude to the wavelength is between about 0.05 and 0.3.

17. The method of claim 14 wherein a force of at least about 0.1 pounds is required to disengage the stiff wavy wire segment from the coil.

\* \* \* \* \*